United States Patent [19]

Hechenbleikner

[11] 4,007,229
[45] Feb. 8, 1977

[54] PREPARATION OF HYDROXYALKYL PHOSPHINE OXIDES AND SULFIDES

[75] Inventor: Ingenuin Hechenbleikner, West Cornwall, Conn.

[73] Assignee: Borg-Warner Corporation, Chicago, Ill.

[22] Filed: Feb. 12, 1975

[21] Appl. No.: 549,405

[52] U.S. Cl. .................. 260/606.5 P; 204/158 R
[51] Int. Cl.² ................... C07F 9/53; B01J 1/10
[58] Field of Search ............... 260/606.5 B

[56] References Cited

UNITED STATES PATENTS

| 3,242,217 | 3/1966 | Hammann et al. | 260/606.5 P |
|---|---|---|---|
| 3,267,149 | 8/1966 | Garner | 260/606.5 P |
| 3,293,302 | 12/1966 | Popoff et al. | 260/606.5 P |
| 3,683,028 | 8/1972 | Haas | 260/606.5 P |
| 3,790,638 | 2/1974 | Kleiner et al. | 260/606.5 P |

FOREIGN PATENTS OR APPLICATIONS

| 1,040,549 | 10/1958 | Germany |
|---|---|---|
| 1,056,125 | 4/1959 | Germany |

OTHER PUBLICATIONS

Hellmann et al., Ann. V659, pp. 49–63 (1962).
Arbuzov et al., Izv. Akad. Nauk SSSR, Otd. Khim. Nauk., (3) pp. 502–506 (1963). Izv. Akad. Nauk. SSSR, Otd. Khim. Nauk., (3) pp. 502–506 (1963).
Arbuzov et al., Nekotorye Voprosy Organicheskoy Khinii, pp. 244–255 (1964).
Arbuzov et al., Iz. Akad. Nauk. SSSR, Ser. Khim, 290 (1962).

*Primary Examiner*—Helen M. S. Sneed
*Attorney, Agent, or Firm*—Joseph Shekleton

[57] ABSTRACT

A process for the preparation of 2-hydroxyalkylphosphine oxides and sulfides. The corresponding 2-acyloxyphosphine is hydrolyzed (or alcoholyzed) and oxidized, in either order, to produce the desired 2-hydroxyalkylphosphine oxide or sulfide. The product may contain one, two or three 2-hydroxyalkyl groups, depending on the phosphine starting material used.

9 Claims, No Drawings

PREPARATION OF HYDROXYALKYL PHOSPHINE OXIDES AND SULFIDES

This invention relates to a process for the preparation of certain phosphine oxides and sulfides. More particularly, it related to such a process wherein one or more hydroxyalkyl groups are attached to the phosphorus atom of the phosphine molecule.

The phosphine oxides and sulfides of this invention are useful as flame-retardant agents and also as intermediates in the preparation of plasticizers. In the latter case, carboxylic acids, anhydrides or acyl chlorides may be reacted with the one or more hydroxyl groups to form the corresponding esters. Moreover, products having surfactant properties may be prepared by reacting alkylene oxides with these hydroxyl groups, so as to form pendant polyoxyalkylene chains.

The preparation of 4-hydroxybutylphosphine oxides and sulfides is shown in U.S. Pat. No. 3,267,149 (Garner). Dihydrocarbon phosphinic halides and dihydrocarbon thiophosphinic halides are reacted with tetrahydrofuran in the presence of a metal catalyst, such as magnesium. The corresponding phosphines undergo the same reaction and the resulting 4-hydroxybutylphosphines can be oxidized with aqueous hydrogen peroxide to the 4-hydroxybutylphoshine oxide.

U.S. Pat. No. 3,683,028 (Haas) shows the preparation of tris(hydroxymethyl)phosphine oxide by a process involving the reaction of water with tris(hydroxymethyl)phosphine, in the presence of small amount of formaldehyde which acts as a catalyst. The reaction is carried out at 100° C – 150° C, preferably in a pressure-resistant vessel.

German Patent No. 1,040,549 (Reuter et al) shows the preparation of tris(hydroxymethyl)phosphine oxide by oxidation of the corresponding phosphine with air at 0°–50° C, followed by removal of solvent in vacuo.

The preparation of hydroxymethyldicyclohexylphosphine oxide and sulfide is shown in Hellmann et al, Ann. 659, 49–63 (1962); dicyclohexylphosphine is reacted either with sulfur (in benzene or ethanol) or oxygen, as the case may be, at elevated temperatures.

An article by Arbuzov et al dealing with the addition of butylphosphine to unsaturated compounds, in Izv. Akad. Nauk. SSSR, Otd. Khim. Nauk. 1963 (3) 502–6, shows the preparation of butyl-di-(3-hydroxypropyl)-phosphine oxide and sulfide. The oxide was prepared by the action of aqueous 330% hydrogen peroxide at temperatures below 60° C. The sulfide was prepared by treatment with sulfur under nitrogen; the reaction is said to be exothermic. In each case yields are reportedly good.

Another Arbuzov et al article, Nikotoryl Vopr. Organ. Khim. Sb. (Kazan: Kazansk. Univ.) 1964, 244–55, also shows the oxidation and sulfurization of butyl-di-(3-hydroxypropyl)phosphine to the corresponding phosphine oxide and phosphine sulfide. Also shown are the oxidation ans sulfurization of the butyl-di-(3-acetoxypropyl)phosphine, as well as the analogous phoshines where phenyl replaces butyl.

A third Arbuzov et al article, in Izv. Akad. Nauk. SSSR, Ser. Khim. (1962) 290–5, also shows the conversion of phenyl-di-(3-acetoxypropyl)phosphine to the corresponding oxide and sulfide. The oxide was obtained by the action either of oxygen at 130° C – 140° C or 30% aqueous hydrogen peroxide at 60° C – 100° C. Sulfurization was effected by heating with sulfur at 150° C for four hours. Similar conversions of phenyl-di-(3-hydroxypropyl)phosphine are shown.

German Patent No. 1,056,125 discloses a method for preparing tris-hydroxymethylphosphine sulfide; the method involves the portionwise addition of a carbon disulfide solution of sulfur to a solution of tris-hydroxymethylphosphine in anhydrous ethanol at a temperature below 40° C.

U.S. Pat. No. 3,247,217 (Hammann et al) deals with the preparation of substantially pure phosphinylidynetrimethanol, i.e., $(HOCH_2)_3P = O$ and trialkanoates thereof, and refers incidentially, at column 2, lines 19–20, to the hydrolysis of the tribenzoate or trilaurate. Hydrolysis of the monoacetate of diphenyl hydroxymethylphosphine oxide, i.e., $(C_2H_5)_2P(O)CH_2OH$, is shown in U.S. Pat. No. 3,293,302 (Popoff et al); this hydrolysis is part of a two-step process whereby hydroxymethylphosphine oxides are prepared.

Nowhere in the prior art, however, is there disclosed a method for preparing 2-hydroxyethylphosphine oxides and sulfides or the 2-hydroxypropyl analogs thereof. It is accordingly a principal object of the present invention to provide such a process.

Another object of the present invention is to provide such a process which utilizes a 2-acetoxyalkylphosphine as a raw material.

These and other objects are accomplished by the invention herein comprising a process for the preparation of hydroxyalkylphosphine oxides and sulfides comprising the steps of (1) alcoholysis or hydrolysis and (2) oxidation, in either order, of an ester-substituted phosphine having the structural formula:

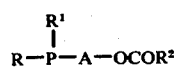

where R and $R^1$ are hydrogen, alkyl, aryl, cycloalkyl, aralkyl or $A—OCOR^2$, A is ethylene or propylene, and $R^2$ is alkyl of 2–17 carbon atoms.

All of the steps contemplated above in the overall process are easily carried out and result in good yields. As noted, the two steps are interchangeable, i.e., the alcoholysis or hydrolysis (as one step) may be carried out first, followed by oxidation, or it may follow the oxidation step. Either arrangement is suitable.

The alcoholysis step is most usually effected by means of an acidic methanol solution. The acyloxyphospine, or acyloxyphosphine oxide or sulfide, simply is dissolved in methanol and a strong mineral acid such as sulfuric or hydrochloric acid, is added. Other alcohols can be used, but preferably those which are sufficiently volatile as to permit easy removal of the resulting ester by-product, i.e., those alcohols having less than eight carbon atoms. The alcoholysis occurs spontaneously at room temperature, and in some instances it is desirable to control the temperature of the reaction mixture by means of external cooling. Where the oxidation step precedes the alcoholysis step it ordinarily is unnecessary to purify the phosphine oxide or sulfide; the crude intermediate product is easily alcoholyzed.

The alcoholysis reaction involves formation of a low-boiling ester, as shown in the following illustrative equation:

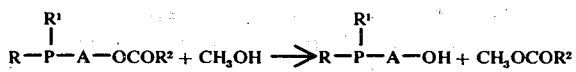

where R, R¹, R² and A are as previously defined. The relatively low-boiling ester, e.g., methyl acetate is removed by distillation.

Hydrolysis of the 2-acyloxyalkylphosphine or phosphine oxide is likewise accomplished by well-known methods, involving either alkaline or acidic media. Mild refluxing with 5% aqueous sodium hydroxide or hydrochloric acid is effective to hydrolyze the acyloxy groups herein.

Sulfurization of the phosphines also is accomplished by methods well-known in the art. The reaction is exothermic and occurs readily at room temperature merely upon mixing the phosphine and elemental sulfur, preferably in a solvent. In some instances the sulfur does not dissolve readily in the solvent or the reaction medium, such that the rate of dissolution of the sulfur is the rate-determining step of the process. If hydrolysis or alcoholysis is the first step, the 2-hydroxyethyl intermediate need not be purified prior to sulfurization.

Oxidation of the phosphine to form the phosphine oxide may be accomplished in any of several known ways. Typically, it involves the action of aqueous alkaline hydrogen peroxide, or other oxidizing agents such as $KM_nO_4$, $PbO_2$, etc. It is also somewhat exothermic.

It will be seen that the chemical reactions of the process herein are not new in themselves except as they apply to the particular reactants and products of the invention. The combinations of such reactions, however, are novel, even in their broader context.

As earlier noted the ester-substituted phosphine employed in the process of this invention has the structural formula:

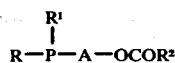

where R and $R_1$ are hydrogen, alkyl, aryl, cycloalkyl, aralkyl or A—$OCOR_2$, A is ethylene or propylene and R² is alkyl of 2-17 carbon atoms. R and R¹ preferably are each less than ten carbon atoms and, more preferably, their total carbon atom content is less than fifteen. Illustrative examples include hydrogen, methyl, ethyl, isopropyl, n-butyl, n-hexyl, isooctyl, 2-ethylhexyl, phenyl, phenethyl, p-tolyl, cyclohexyl and cyclopentyl.

A in the above structural formula is either ethylene or propylene. As such it is the residue of the vinyl group of a vinyl acylate, e.g., vinyl acetate or isopropenyl acetate.

R² in that structural formula is alkyl. Illustrative examples include methyl, ethyl, n-propyl, n-amyl, 2-ethylamyl, n-nonyl, n-undecyl and n-heptadecyl. Preferably, though, R² contains fewer than six carbon atoms, so that the alkyl radical which it provides on alcoholysis contributes to the formation of a relatively volatile by-product ester, which is thereby easily removed from the alcoholysis mixture. Thus, if R² is methyl and the alcohol used in the alcoholysis reaction is methanol, the resulting by-product ester is methyl acetate, which distills at 60° C.

As indicated, R and R¹ can also be A—OCOR². That is, the ester-substituted phosphine may be a diester or triester. The ester-substituted phosphines of the invention are prepared by reaction of a phosphine containing at least one phosphorus to hydrogen (P-H) linkage with a vinyl ester, e.g.,

It will be seen that the use of three moles of vinyl acetate in the above equation will give rise to the triester instead of the monoester, and such triester, as well as the diester, is contemplated within the scope of this invention. Moreover, ester-substituted phosphines may be prepared also from monoalkyl and monoaryl phosphines, for example, and the diester-substituted products available from these are also contemplated within the scope of this invention. The reaction product of phenyl phosphine and isopropenyl acetate is illustrative:

The invention is illustrated by the following examples which of course are not limiting in any respect.

EXAMPLE 1

A solution of 258 g. (3.0 moles) of vinyl acetate and 0.5 g. of azo bis-isobutyronitrile in 300 ml. of benzene is prepared and evacuated to the point at which the benzene begins to boil, whereupon phosphine is bubbled in throughout a period of four hours. The mixture is exposed to sunlight all the while. Benzene is then removed at 20° C/15 mm., care being taken to avoid any higher temperature so as to avoid polymerization, leaving as the residue a quantitative yield of tris2-acetoxyethylphosphine.

EXAMPLE 2

A solution of 58.4 g. (0.2 mole) of tris-2-acetoxyethylphosphine in 100 ml. of benzene is treated with 6.7 g. (0.21 mole) of finely powdered sulfur. The sulfur dissolves slowly in the benzene and the sulfurization is complete when all the sulfur has disappeared. The phosphine sulfide is isolated by distilling away the benzene, leaving a substantially quantitative yield of tris-2-acetoxyethylphosphine sulfide. This product is treated with a molar excess of methanol and 0.5 g. of sulfuric acid, then stripped of methyl acetate and methanol, leaving as the viscous, light yellow, oily residue, a quantitative yield of the desired tris-2-hydroxyethylphosphine sulfide.

EXAMPLE 3

A solution of 58.4 g. (0.2 mole) of tris-2-acetoxyethylphosphine in 100 ml. of methanol is treated with 0.1 g. of sodium carbonate, then with 0.2 mole of 50% aqueous hydrogen peroxide. The mixture is stirred and cooled (externally) throughout these steps, at the conclusion of which the oxidation to the phosphine oxide is complete. Thereupon, 0.5 g. of 85% sulfuric acid is added, with continued stirring, and methyl acetate and methanol stripped, leaving as the residue a quantitative yield of tris-2-hydroxyethylphosphine oxide.

EXAMPLE 4

A mixture of 49.2 g. (0.2 mole) of diisobutyl 2-acetoxypropylphosphine, 6.4 g. (0.2 mole) of sulfur and 150 ml. of toluene is stirred for two hours during which time the temperature rises 5° C from room temperature. At the end of this period all of the sulfur is reacted. The toluene is removed by distillation at 15 mm. pressure on a steam bath. The residue is a colorless liquid which, upon testing with a benzene solution of iodine, is shown to contain no phosphine. This product then is dissolved in 150 ml. of methanol, treated with 0.5 g. of p-toluenesulfonic acid and transesterified as in Example 2. The diisobutyl 2-hydroxyethylphosphine sulfide is obtained as colorless, viscous liquid.

EXAMPLE 5

A solution of 28.2 g. (0.1 mole) of phenyl bis(2-acetoxyethyl)phosphine and 1 ml. of triethylamine in 150 ml. of acetone is stirred at 20°–30° C for 30 minutes during which time 6.9 g. (0.11 mole) of 50% aqueous hydrogen peroxide is added portionwise to the mixture. External cooling is necessary to maintain the above temperature. The acetone then is removed leaving a colorless, viscous oil which is insoluble in water. This phenyl bis(2-acetoxyethyl)phosphine oxide is converted to the corresponding phenyl bis(2-hydroxyethyl)phosphine oxide by transesterification with methanol as in Example 2. The desired product is a colorless, water-soluble oil.

EXAMPLE 6

A solution of 40.2 g. (0.1 mole) dodecyl bis (2-acetoxyethyl phosphine and 0.2 g. of p-toluenesulfonic acid in 100 ml. of methanol is heated and distilled through a 15-plate distillation column to remove a methyl acetate-methanol (81.3% - 18.7%) azeotrope at 54° C. The distillation is continued until the distillation temperature reaches 65° C, the boiling point of methanol. The column then is removed and 1 g. of sodium carbonate is added. Then, 6.9 g. of 50% aqueous hydrogen peroxide is added portionwise over a period of 20 minutes, the temperature being maintained at 20°–30° C by means of an ice bath. The mixture is filtered to remove the sodium carbonate, then freed of methanol by stripping at 15 mm. leaving a light-colored viscous oil.

I claim:

1. A process for the preparation of hydroxyalkylphosphine oxides and sulfides comprising the steps of (1) alcoholysis and (2) oxidation, of an ester-substituted phosphine having the structural formula:

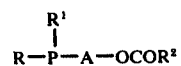

where R and R¹ are hydrogen, alkyl, aryl, cycloalkyl, aralkyl or A—OCOR², A is ethylene or propylene, and R² is alkyl of 2–17 carbon atoms.

2. A process for the preparation of hydroxyalkylphosphine oxides and sulfides comprising the steps of (1) hydrolysis and (2) oxidation, of an ester-substituted phosphine having the structural formula:

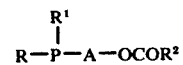

where R and R¹ are hydrogen, alkyl, aryl, cycloalkyl, aralkyl or A—OCOR², A is ethylene or proylene, and R² is alkyl of 2–17 carbon atoms.

3. The process of claim 1 wherein the alcoholysis reaction involves a transesterification with an alcohol having less than 8 carbon atoms.

4. The process of claim 1 wherein the oxidation step is a sulfurization reaction.

5. The process of claim 2 wherein the oxidation step is a sulfurization reaction.

6. A process for the preparation of hydroxyalkylphosphine oxides and sulfides comprising the steps of (1) oxidation and (2) alcoholysis, of an ester-substituted phosphine having the structural formula:

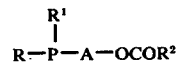

where R and R¹ are hydrogen, alkyl, aryl, cycloalkyl, aralkyl or A—OCOR², A is ethylene or propylene, and R² is alkyl of 2–17 carbon atoms.

7. A process for the preparation of hydroxyalkylphosphine oxides and sulfides comprising the steps of (1) oxidation and (2) hydrolysis, of an ester-substituted phosphine having the structural formula:

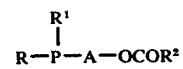

where R and R¹ are hydrogen, alkyl, aryl, cycloalkyl, aralkyl or A—OCOR², A is ethylene or propylene, and R²is alkyl of 2–17 carbon atoms.

8. The process of claim 6 wherein the oxidation step is a sulfurization reaction.

9. The process of claim 7 wherein the oxidation step is a sulfurization reaction.

* * * * *